US005516442A

United States Patent [19]

Russo et al.

[11] Patent Number: 5,516,442

[45] Date of Patent: May 14, 1996

[54] POLYMERIC THIOHETEROCYCLIC RUST AND CORROSION INHIBITING MARINE DIESEL ENGINE LUBRICANT ADDITIVES

[75] Inventors: Joseph M. Russo, Poughkeepsie; Rodney L. Sung, Fishkill; Benjamin J. Kaufman, Hopewell Jct., all of N.Y.; Thomas F. Derosa, Passaic, N.J.

[73] Assignee: Texaco Inc., White Plains, N.Y.

[21] Appl. No.: 514,155

[22] Filed: Aug. 11, 1995

Related U.S. Application Data

[63] Continuation of Ser. No. 263,269, Jun. 21, 1994, abandoned, which is a continuation of Ser. No. 938,799, Sep. 1, 1992, abandoned.

[51] Int. Cl.[6] .................... C10M 135/36; C07D 225/02; C07D 285/12

[52] U.S. Cl. ........................ 252/47.5; 540/463; 540/524; 548/139

[58] Field of Search .......................... 252/47.5; 548/139; 540/463, 524

[56] References Cited

U.S. PATENT DOCUMENTS

| | | | |
|---|---|---|---|
| 4,845,230 | 7/1989 | Kume et al. | 548/139 |
| 4,902,804 | 2/1990 | King et al. | 252/47.5 |
| 4,990,652 | 2/1991 | King et al. | 560/192 |

*Primary Examiner*—Jerry D. Johnson

[57] ABSTRACT

A rust and corrosion inhibiting marine diesel engine lubricating oil additive is provided which comprises a mixture of:

(a) an oligomeric polythiocyclic imide represented by the formula

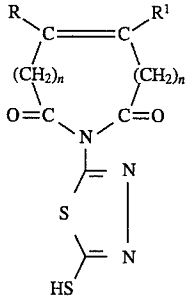

wherein R and $R^1$ each are a ($C_1$–$C_{50}$) saturated or unsaturated aliphatic group and n is an integer of 0 to 5; an oligomeric amine represented by $R''—NH_2$ where R" is dodecyl or a ($C_{12}$–$C_{25}$) alkyl group; and either (b) a polymeric additive of a poly [ethylene-co-propylene)-g-succinic anhydride] represented by the formula

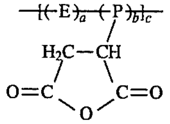

wherein ethylene (E) and propylene (P) are randomly incorporated; a and b correspond to 60 mole % and 40 mole %, respectively; and the repeat unit, c, is an integer of 40 to 40,000 so that the overall molecular weight of said succinic anhydride is 50,000 to 70,000 AMU's and an (c) amino thiocyclic represented by the formula

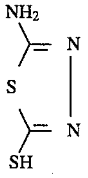

2 Claims, No Drawings

POLYMERIC THIOHETEROCYCLIC RUST AND CORROSION INHIBITING MARINE DIESEL ENGINE LUBRICANT ADDITIVES

This is a continuation of application Ser. No. 08/263,269, filed on Jun. 21, 1994, now abandoned which is a continuation of application Ser. No. 07/938,799, filed on Sep. 1, 1992 now abandoned.

BACKGROUND OF THE INVENTION

This invention relates to a lubricant additive which imparts enhanced rust and corrosion resistance to engine lubricating oils, and to a lubricating oil composition containing such an additive. More specifically, this invention relates to a marine diesel engine lubricant additive comprising a polythiocyclic imide and a poly[(ethylene-co-propylene-g-succinic anhydride].

The primary function of lubricants is to decrease friction. Frequently, however, lubricating oils need additional properties, such as oxidation and corrosion resistance, to be used effectively. For example, lubricants used in the crankcases of large diesel engines, such as marine and railway diesel engines, are often subjected to operating conditions requiring special considerations. In particular, poor grade fuels, such as marine residual fuel, can be mixed with regular diesel fuel, such as D-2, for fuel cost savings. However, engine performance problems, such as increased corrosion and poor oxidative stability, often arise. Additionally, new and more fuel efficient railway diesel engines place greater mechanical and chemical demands on the oxidation and corrosion resistance of lubricants. Lubricants used for such newer engines are typically changed more frequently or reformulated to limit corrosion, since, once oxidized, lubricants cause increased engine corrosion.

Various additives have been used to improve the rust and corrosion inhibition of lubricants. For example, calcium sulfurized alkyl phenolates have been effective oxidation and corrosion inhibitors. These compounds are typically made by processes including expensive recovery procedures and hazardous byproducts which are difficult to dispose of in an environmentally sound way. Alternatively, calcium sulfurized phenolates, made by a process using lime as the calcium source to avoid such processing problems, fail to provide a high level of rust and corrosion inhibition.

Lubricants used in the crankcase of a slow speed cross-headed marine engine must protect the engine parts from corrosion and especially rust. Rust is produced when ferrous metal engine components come in aliphatic with water; typically through two avenues. The first involve the internal combustion process where water is produced; the second from outside sources, that is, fresh water or saline water. In both cases, however, the net effect is identical: rust and corrosion that reduce engine efficiency and lifetime.

Rust and corrosion inhibitors are added to lubricating oils as part of the overall additive package comprising between 0.5 weight percent to perhaps as much as 2.5 weight percent. Ideally, rust and corrosion additives should be completely miscible with lubricating oils. Moreover, it is essential that these materials are completely compatible with other additives therein the lubricating oil. Rust or corrosion inhibitor additives that interact with other lubricating components are of little concern unless an aesthetically unappealing appearance results. This incompatibility with either the lubricating oil itself or additives therein is generally manifested by haze or solution turbidity. Despite the identical performance of both turbid and clear lubricating oil blends, consumer-perceived product imperfection will mar successful marketing of the oil blends.

Various additives have been used to improve the oxidation and corrosion resistance of lubricants. For example, calcium sulfurized alkyl phenolates have been effective oxidation and corrosion inhibitors. These compounds are typically made by processes including expensive recovery procedures and hazardous by products which are difficult to dispose of in an environmentally sound way. Alternatively, calcium sulfurized phenolates, made by a process using lime as the calcium source to avoid such processing problems, fail to provide a high level of oxidation and corrosion resistance.

Thus, there is a need for a lubricant additive which will provide effective oxidation and corrosion resistance, without posing the environmental hazards of other oxidation and corrosion inhibitors.

Therefore, it is an object of the present invention to provide both an additive composition and a lubricating oil composition which have significant oxidation and corrosion resistance.

SUMMARY OF THE INVENTION

The present invention provides a lubricating oil additive composition which imparts rust and corrosion inhibition to marine diesel lubricating oil, and a lubricating oil composition containing such an additive.

The lubricating oil additive of the present invention comprises:

(a) a polythiocyclic imide represented by the formula

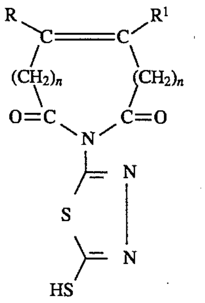

wherein R and $R^1$ each are a ($C_1$–$C_{50}$) saturated or unsaturated aliphatic group and n is an interger of 0 to 5; or (b) a poly [(ethylene-co-propylene)-g-succinic anhydride], EPSA, represented by the formula

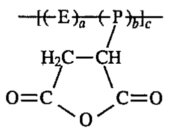

wherein ethylene (E) and propylene (P) are randomly incorporated; a and b correspond to 60 mole % and 40 mole %, respectively; and the repeat unit, c, is an integer of 40 to 40,000 so that the overall molecular weight of said succinic anhydride is 50,000 to 70,000 AMU's.

The repeat unit, c is preferably an integer of 200 to 500.

The present invention also provides a lubricating oil composition comprising a major portion of a hydrocarbon lubricating oil and a minor effective portion, sufficient to impart rust and corrosion inhibition to the lubricating oil composition of the additive composition described above.

DETAILED DESCRIPTION OF THE INVENTION

The lubricant additive of the present invention comprises a polythiocyclic imide or a poly [(ethylene-co-propylene-g-succinic anhydride]. The polythiocyclic imide component is represented by the general formula

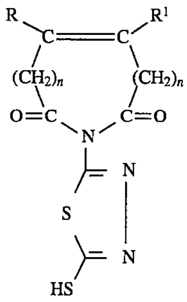

wherein R and $R^1$ each are a ($C_1$–$C_{50}$) saturated or unsaturated aliphatic group and n is an integer of 0 to 5.

The poly[ (ethylene-co-propylene)-g-succinic anhydride] reactant is represented by the general formula

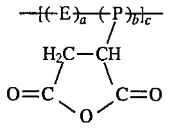

wherein ethylene (E) and propylene (P) are randomly incorporated; a and b correspond to 60 moles % and 40 mole %, respectively; and the repeat unit, c, is an integer of 40 to 40,000 so that the overall molecular weight of said succinic anhydride is 50,000 to 70,000 AMU's; or an oligomeric amine represented by the formula $$R''-NH_2$$

where R" is dodecyl or a ($C_{12}$–$C_{25}$) alkyl group.

In preparing the present lubricant additives, one or two processing steps may be necessary to generate the active lubricating oil component; examples of both, however, are as follows:

Step 1. Preparation of the polythiocyclic imide as shown below in Equation (EQ.) 1;

Step 3 Incorporation of a polythiocyclic made using poly[(ethylene-co-propylene)-g-succinic anhydride], said succinic anhydride as shown below in Equation (EQ.) 3;

EQ.1

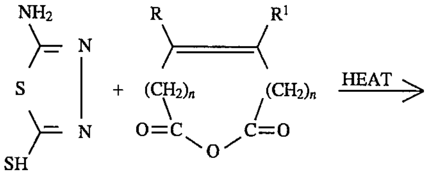

-continued

EQ.1

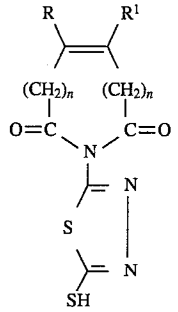

EQ.3

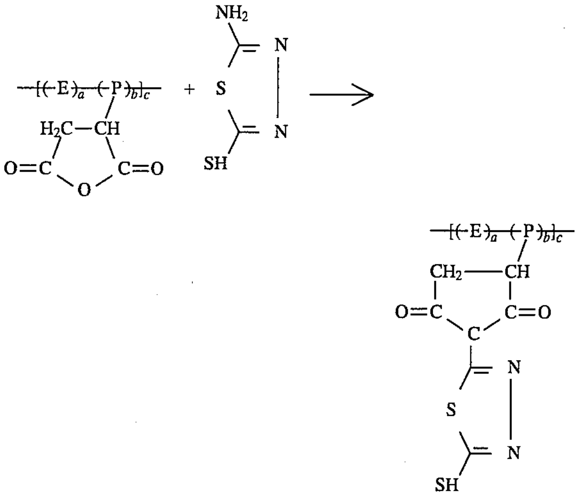

In the above Equations (EQS.) 1 and 3, R and $R^1$ each are a ($C_1$–$C_{50}$) saturated or unsaturated aliphatic group; n is an integer of 0 to 5; and (E) and (P) and integers a, b and c are as defined above.

TESTING RESULTS

Testing results correlating haze-free blending and rust inhibition properties are provided below in Table I.

The lubricating oil composition of the present invention may be made by any procedure suitable for making lubricating oil compositions. Typically, the additive is added to the lubricant by simply mixing the components together, producing a lubricant with increased oxidation and corrosion resistance.

Though the thioheterocyclics are extremely cost effective corrosion inhibitors, they are, however, insoluble in most non-polar media, most notably oil.

Thus, two oil solubilizing agents that were used, include:

a) A saturated acyclic aliphatic chain. Subsequent incorporation of this material into the experimental intermediate generated a MONOMERIC thioheterocyclic additive; and b) A polymeric ethylene-propylene copolymer. This was obtained using poly[(ethylene-co-propylene)-g-succinic anhydride]; EPSA. Use of poly(ethylene-co-propylene) as an oil solubilize generated to the corresponding POLYMERIC thioheterocyclic additive.

These different oil solubilizers (i.e., "a" and "b") are, respectively, illustrated below.

(a) MONOMERIC THIOHETEROCYCLIC ADDITIVE

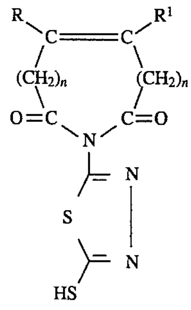

wherein R and $R^1$ each are a ($C_1$–$C_{50}$) saturated or unsaturated aliphatic group; n is an integer of 0 to 5

(b) POLYMERIC THIOHETEROCYCLIC ADDITIVE

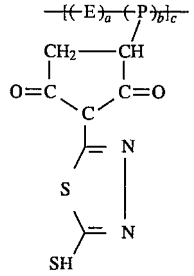

where ethylene (E) and propylene (P) are randomly incorporated; a and b correspond to 60 mole % and 40 mole %, respectively; and, the repeat unit, c, is 40 to 40,000 so that the overall molecular weight of said succinic anhydride is 50,000 to 70,000 AMU's.

The additive of the present invention may be added to the base lubricating oil in any minor, effective, corrosion and oxidation inhibiting amounts. Preferably the additive will be added to the base lubricating oil in amounts of about 0.1 to about 5 wt. % based on the weight of the lubricating oil. More preferably the effective amount is abut 1 wt. % to about 2 wt. % based upon the weight of the lubricating oil. The additive mixture may be added separately, or as a component of an additive package which contains other additives. Such other materials, include, among others, one or more of the following: dispersants, detergents, viscosity index improvers, anti-foamants, antiwear agents, demulsifiers, other anti-oxidants, other corrosion inhibitors, and other materials useful in lubricants. Preferred optional additives or additive packages include: ORONITE® 2939 and the like, manufactured and sold by Chevron Chemical Company of Irvine, Calif. The amount of such materials may be any desired amounts which provide the desired properties.

According to the present invention, a thioheterocyclic has been discovered that upon dissolution in lubricating oil reduces corrosion and rust while the oil remains turbid-free. Turbid free oils solution involve the introduction of hydrophobic oil solubilizers.

The present invention offers two clear advantages over existing technology. These include:

1. Processes and chemical technology that is extremely cost effective; and
2. Products are haze or turbid-free.

As indicated above, in order to show the effectiveness of the additives of this invention, the results of testing the additive are provided below in Table I. The results show correlating haze-free blending and rust inhibition properties of the additive-containing additives.

TABLE I

Summary of ASTM Salt Water Test And Corresponding Hazetrom Turbidity For Modified And Experimental Lubricating Oil Blends

| | LUBRICATING OILS | | | |
|---|---|---|---|---|
| Components | Oil Sample Containing Rust Inhibitor (Wt. %) | Oil Sample Not Containing Inhibitor (Wt. %) | Oil Sample Containing Experimental Monomeric Additive | Oil Sample Containing Experimental Polymeric Additive |
| SNO-20G DTA | 39.30 | 39.30 | 39.30 | 39.30 |
| SNO-50 DTA | 55.80 | 56.15 | 55.15 | 55.15 |
| Oronite 218A | 3.60 | 3.60 | 3.60 | 3.60 |
| TLA-111B | 0.65 | 0.65 | 0.65 | 0.65 |
| Vanlube NA | 0.30 | 0.30 | 0.30 | 0.30 |
| TX-1416 (ppm) | 150 | 150 | 150 | 150 |
| Surfonic N-60 | 0.35 | — | — | — |
| Hazetron Turbidity | 55 | 9 | 5 | 7 |
| ASTS Salt Water Test (D665) | Pass | Fail | Pass | Pass |

Although this invention has been illustrated by reference to specific embodiments, it will be apparent to those skilled in the art that various changes and modifications may be made which clearly fall within the scope of this invention.

The lubricating oil composition of the present invention is advantageous in that it has superior anti-oxidancy and anti-corrosion properties. The advantages of the instant invention in increasing oxidation and corrosion resistance have been shown by a comparison of the lubricating oil compositions as provided below in Table II.

TABLE II

| Component | Reference (Wt. %) | Example 1 (Wt. %) | Example 2 (Wt. %) | Example 3 (Wt. %) | Example 4 (Wt. %) |
|---|---|---|---|---|---|
| N 300 Pale Oil | 14.4 | 14.1 | 14.1 | 14.1 | 14.1 |
| N 900 Pale Oil | 70.55 | 69.6 | 69.6 | 69.6 | 69.6 |
| Polyethyl | 0.3 | 0.3 | 0.3 | 0.3 | 0.3 |
| Methacryate detergent[1] | 14.75 | 14.5 | 14.5 | 15.0 | 15.0 |
| Experimental Additive | — | 1.0 | 1.0 | 1.0 | 1.0 |

[1]Oronite 2939, available from the Chevron Oil Company of Irvine, California

Although this invention has been illustrated by reference to specific embodiments, it will be apparent to those skilled in the art that various changes and modifications may be made which clearly fall within the scope of this invention.

We claim:

1. A lubricating oil additive which comprises (a) a polythiocyclic imide represented by the formula

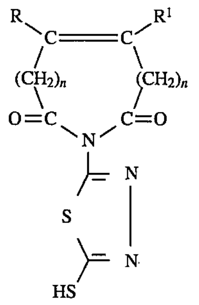

wherein R and $R^1$ each are a ($C_1$–$C_{50}$) saturated or unsaturated aliphatic group and n is an integer of 0 to 5.

2. A lubricating oil composition comprising:

(a) a major portion of a hydrocarbon lubricating oil; and (b) a minor portion, sufficient to impart rust and corrosion inhibitions to the lubricating oil composition, of a lubricating oil additive which comprises (1) a polythiocyclic imide represented by the formula

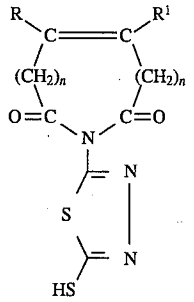

wherein R and $R^1$ each are a ($C_1$–$C_{50}$) saturated or unsaturated aliphatic group and n is an integer of 0 to 5.

* * * * *